US 6,245,107 B1
Jun. 12, 2001

(54) METHODS AND APPARATUS FOR TREATING DISC HERNIATION

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 09/322,516

(22) Filed: May 28, 1999

(51) Int. Cl.⁷ .............................. A61F 2/44; A61B 17/56
(52) U.S. Cl. ............................................... 623/17; 606/61
(58) Field of Search ...................... 623/17, 18; 606/61, 606/60; 128/898

(56) References Cited

U.S. PATENT DOCUMENTS

| | | | |
|---|---|---|---|
| 4,413,359 | 11/1983 | Akiyama et al. | 3/1 |
| 4,512,338 | 4/1985 | Balko et al. | 128/1 R |
| 4,663,358 | 5/1987 | Hyon et al. | 521/64 |
| 4,772,287 | 9/1988 | Ray et al. | 623/17 |
| 4,834,757 | 5/1989 | Brantigan | 623/17 |
| 4,904,260 | 2/1990 | Ray et al. | 623/17 |
| 4,932,969 * | 6/1990 | Frey et al. | 623/17 |
| 5,015,255 | 5/1991 | Kuslich | 623/17 |
| 5,047,055 | 9/1991 | Bao et al. | 623/17 |
| 5,100,422 | 3/1992 | Berguer et al. | 606/151 |
| 5,147,374 | 9/1992 | Fernandez | 606/151 |
| 5,171,278 | 12/1992 | Pishrodl | 623/17 |
| 5,192,326 * | 3/1993 | Bao et al. | 623/17 |
| 5,258,043 | 11/1993 | Stone | 623/66 |
| 5,304,194 | 4/1994 | Chee et al. | 606/191 |
| 5,342,394 | 8/1994 | Matsuno et al. | 606/213 |
| 5,370,660 | 12/1994 | Weinstein et al. | 606/215 |
| 5,390,683 | 2/1995 | Pisharodi | 128/898 |
| 5,425,772 | 6/1995 | Brantigan | 623/17 |
| 5,540,715 | 7/1996 | Katsaros et al. | 606/213 |
| 5,545,229 | 8/1996 | Parsons et al. | 623/17 |
| 5,562,736 | 10/1996 | Ray et al. | 623/17 |
| 5,645,597 | 7/1997 | Krapiva | 623/17 |
| 5,681,310 | 10/1997 | Yuan et al. | 606/61 |
| 5,716,416 | 2/1998 | Lin | 623/17 |
| 5,800,549 | 9/1998 | Bao et al. | 623/17 |
| 5,800,550 | 9/1998 | Sertich | 623/17 |
| 5,824,093 * | 10/1998 | Frey et al. | 623/17 |
| 5,827,328 | 10/1998 | Butterman | 623/17 |
| 5,879,366 | 3/1999 | Shaw et al. | 606/213 |
| 5,916,225 | 6/1999 | Kugel | 606/151 |
| 5,976,174 | 11/1999 | Ruiz | 606/213 |
| 5,976,186 | 11/1999 | Bao et al. | 623/17 |
| 6,024,754 | 2/2000 | Engelson | 606/213 |

* cited by examiner

*Primary Examiner*—Henry J. Recla
*Assistant Examiner*—(Jackie) Tan-Uyen T. Ho
(74) *Attorney, Agent, or Firm*—Gifford, Krass, Groh, Sprinkle, Anderson & Citkowski, PC

(57) ABSTRACT

Methods and apparatus for treating disc herniation provide a conformable device which assumes a first shape associated with insertion and a second shape or expanded shape to occlude the defect which typically follows partial discectomy. The device may take different forms including patches size to cover the defect or plugs adapted to fill the defect. In a preferred embodiment, however, the device is a gel or other liquid or semi-liquid which solidifies to occlude the defect from within the body of the disc itself. In another preferred embodiment, a mesh screen is collapsed into an elongated form for the purposes of insertion, thereby minimizing the size of the requisite incision while avoiding delicate surrounding nerves. Such a configuration also permits the use of instrumentation to install the device, including, for example, a hollow tube or sheath adapted to hold the collapsed screen, and a push rod to expel the collapsed device out of the sheath for use in occluding the disc defect. A device may further include one or more anchors to assist in permanently affixing the device with respect to the defect.

14 Claims, 5 Drawing Sheets

METHODS AND APPARATUS FOR TREATING DISC HERNIATION

FIELD OF THE INVENTION

This invention relates generally to the prosthetic appliances and, in particular, to devices for occluding intervertebral disc defects and instrumentation associated with introducing the such devices.

BACKGROUND OF THE INVENTION

Several hundred thousand patients undergo disc operations each year. Approximately five percent of these patients will suffer recurrent disc herniation, which results from a void or defect which remains in the outer layer (annulus fibrosis) of the disc after surgery involving partial discectomy.

Reference is made to FIG. 1A, which illustrates a normal disc as viewed from the feet of a patient up toward the head. The nucleus pulposus 102 is entirely surrounded by the annulus fibrosis 104 in the case of healthy anatomy. Also shown in this cross section is the relative location of the nerves 106. FIG. 1B illustrates the case of the herniated disc, wherein a portion of the nucleus pulposus has ruptured through a defect in the annulus fibrosis, resulting in a pinched nerve 110. This results in pain and further complications, in many cases.

FIG. 1C illustrates the post-operative anatomy following partial discectomy, wherein a space 120 remains adjacent a hole or defect in the annulus fibrosis following removal of the disc material. The hole 122 acts as a pathway for additional material to protrude into the nerve, resulting in the recurrence of the herniation. Since thousands of patients each year require surgery to treat this condition, with substantial implications in terms of the cost of medical treatment and human suffering, any solution to this problem would welcomed by the medical community.

SUMMARY OF THE INVENTION

The subject invention resides in methods and apparatus for treating disc herniation, which may be defined as the escape of nucleus pulposus through a void or defect in the annulus fibrosis of a spinal disc situated between upper and lower vertebra. The invention is particularly well suited to the minimization and prevention of recurrent disc herniation, in which case the defect is a hole or void which remains in the annulus fibrosis following disc operations involving partial discectomy.

In broad, general terms, to correct defects of this type, the invention provides a conformable device which assumes a first shape associated with insertion and a second shape or expanded shape to occlude the defect. The device may take different forms according to the invention, including solidifying gels or other liquids or semi-liquids, patches sized to cover the defect, or plugs adapted to fill the defect.

The device is preferably collapsible into some form for the purposes of insertion, thereby minimizing the size of the requisite incision while avoiding delicate surrounding nerves. Such a configuration also permits the use of instrumentation to install the device, including, for example, a hollow tube and a push rod to expel the device or liquefied material out of the sheath for use in occluding the disc defect.

A device according to the invention may further include one or more anchors to assist in permanently affixing the device with respect to the defect. For example, in the embodiment of a mesh screen, the anchors may assume the form of peripheral hooks configured to engage with the vertebra on either side of the disc. The invention further contemplates a distracting tool used to force the anchors into the vertebra. Such a tool would preferably feature a distal head portion conformal to the expanded shape of the device, enabling the surgeon to exert force on the overall structure, thereby setting the anchors.

DETAILED DESCRIPTION OF THE INVENTION

Figure 1A:
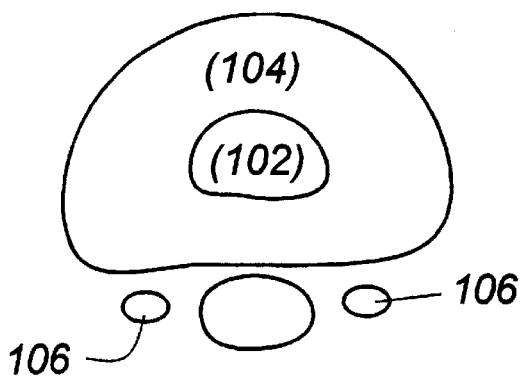
FIG. 1A is a cross section of a human disc exhibiting normal anatomy.
Figure 1B:
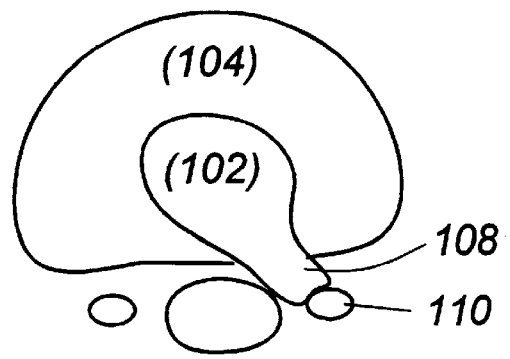
FIG. 1B is a cross section used to illustrate a disc herniation.
Figure 1C:
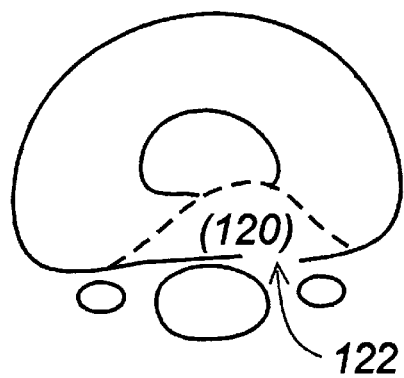
FIG. 1C is a drawing of a disc following a partial discectomy, showing how a space or void remains in the annulus fibrosis.
Figure 2:
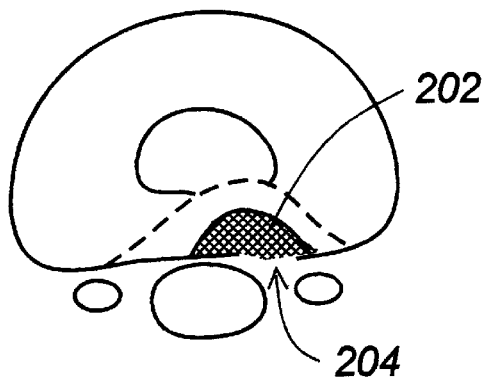
FIG. 2 is a drawing which illustrates a preferred embodiment of the invention in the form of a flexible stent used to occlude a defect in the annulus fibrosis to minimize recurrent disc herniation.

Having discussed the problems associated with postoperative partial discectomy with respect to FIGS. 1A–1C, reference will now be made to FIG. 2, which illustrates a preferred embodiment of the invention, wherein a device in the form of a stent 202 is used to occlude a defect 204 in a human disc, as shown. In this preferred embodiment, the device is composed of a flexible material, which may be cloth, polymeric or metallic. For reasons discussed below, a titanium mesh screen is preferred with respect to this embodiment of the invention.

A flexible device is also preferred because the surgeon is presented with a very small working area. The incision through the skin is typically on the order of 1 to 1.5 inches in length, and the space at the disc level is approximately 1 centimeter on the side. As a consequence, the inventive device and the tools associated with insertion and fixation described below must be sufficiently narrow to fit within these confines.

Figure 3A:
FIG. 3A is a drawing of an applicator used to insert the flexible mesh stent embodiment of FIG. 2.
Figure 3B:
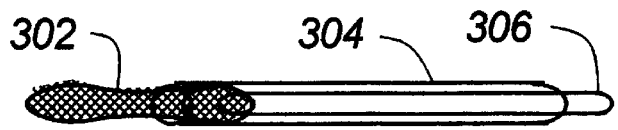
FIG. 3B shows the applicator of FIG. 3A with the stent partially expelled.
Figure 3C:
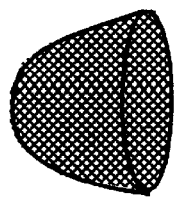
FIG. 3C illustrates a fully expanded shape assumed by the device of FIG. 2 following removal of the insertion tool.

As shown in FIGS. 3A–3C, a flexible screen enables the device to be collapsed into an elongated form 302, which, in turn, facilitates introduction into a sheath 304 associated with insertion. A push rod 306 may then be introduced into the other end of the sheath 304, and either the sheath pulled backwardly or the push rod pushed forwardly, or both, resulting in the shape shown in FIG. 3C, now suitable for implantation.

Figure 4A:
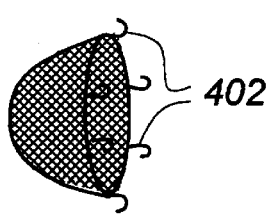
FIG. 4A illustrates the addition of optional peripheral anchors around the stent in the FIG. 4 to assist in fixation.
Figure 4B:
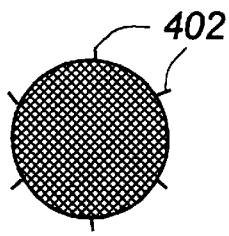
FIG. 4B is an end view of the device of FIG. 4A including the peripheral anchors.
Figure 5:
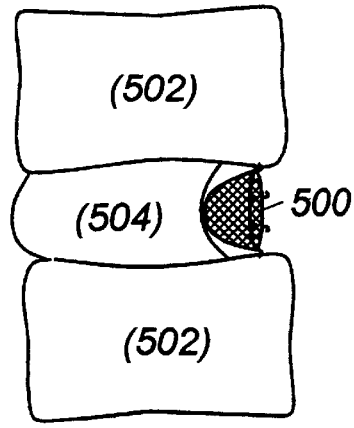
FIG. 5 is a side-view drawing of the device of FIGS. 4A and 4B anchored into upper and lower vertebra bounding the herniated disc.

To further assist in fixation with respect to the surrounding physiology, anchors 402 may be provided around a peripheral edge of the device, as shown in FIG. 4A. FIG. 4B shows an end view of the device of FIG. 4A, and FIG. 5 illustrates the device with anchors generally at 500, being fixed relative to a defective disc 504 bounded by upper and lower vertebrae at 502. It will be apparent to those of skill that each of the devices disclosed herein may be made in different sizes, having varying peripheral dimensions, for example, to match differently sized defects.

Figure 6A:
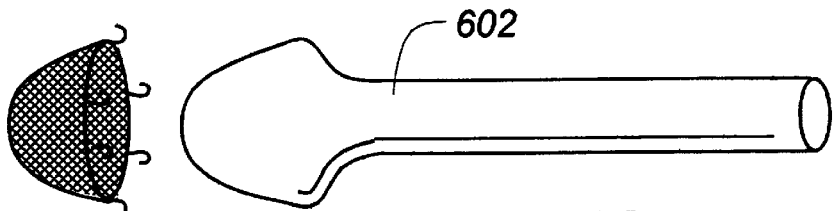
FIG. 6A illustrates an optional distraction tool used to set the anchors of the device of FIGS. 4 and 5 into the vertebra.
Figure 6B:
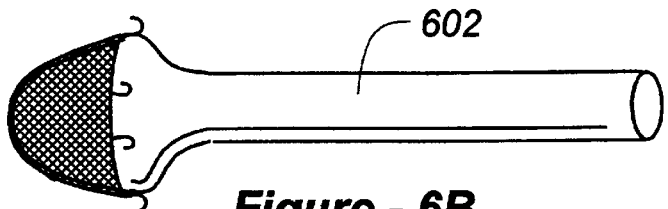
FIG. 6B shows how the distracting tool would be inserted into the device to effectuate distraction.

FIGS. 6A and 6B illustrate how a distracting tool 602 may be used to force the anchors into the vertebrae. That is, having introduced the device into the approximate area, the tool 602, having a forward shape corresponding to that of the expanded mesh shape, may be introduced therein, as shown in FIG. 6B. With force being applied to the tool 602, the anchors may be permanently set into the surrounding bone/tissue.

Figure 7A:
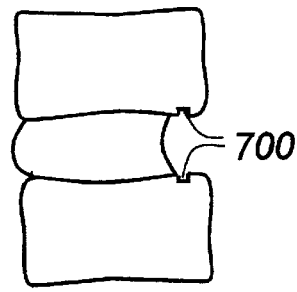
FIG. 7A is a side-view drawing in partial cross-section illustrating the way in which notches may be made to adjoining vertebra to receive a device according to the invention.
Figure 7B:
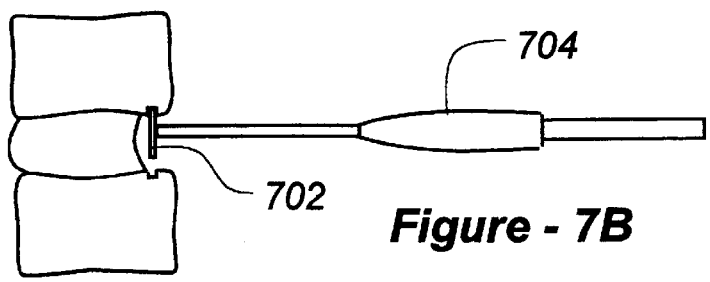
FIG. 7B is a drawing of a tool which may be used to form the notches depicted in FIG. 7A.
Figure 7C:
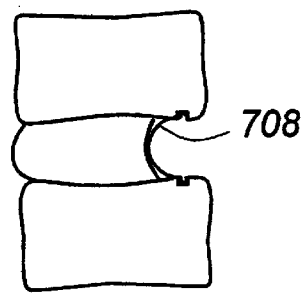
FIG. 7C illustrates the way in which a flexible body may be retained by the notches described with respect to FIGS. 7A and 7B.

FIG. 7A illustrates an alternative approach to fixation, wherein one or more notches 700 may be made into the upper and lower vertebra, preferably through the use of an air-operated drill 704 shown in FIG. 7B, having a cutting wheel 702 adapted for such a purpose. FIG. 7C illustrates the way in which a flexible body 708 may be retained by the notches 700 described with respect to FIGS. 7A and 7B.

Figure 8:
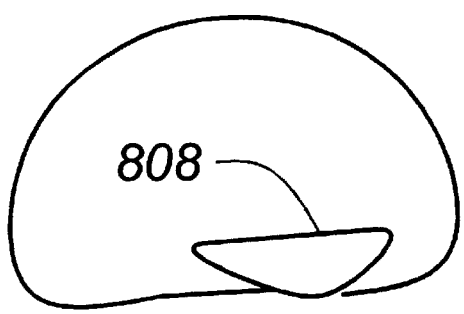
FIG. 8 illustrates an alternative orientation of a flexible body having a convex surface facing outwardly with respect to the wall of the disc being repaired.

FIG. 8 illustrates an alternative orientation of a flexible body having a convex surface facing outwardly with respect to the wall of the disc being repaired.

Figure 9A:
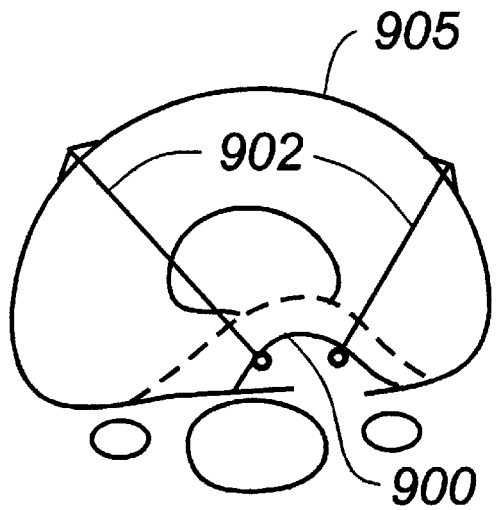
FIG. 9A illustrates how the device according to the invention may be fixed with anchors that penetrate through the disc to be captured at the outer wall thereof.
Figure 9B:
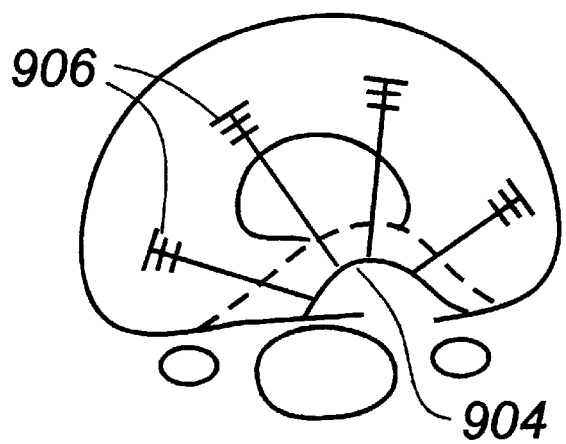
FIG. 9B illustrates an alternative use of anchors which remain within the body of the disc material and do not penetrate its outer wall.

FIG. 9A illustrates a further alternative associated with fixation wherein anchors 902 which penetrate the outer wall of the disc 905 are used to hold a flexible repair device 900 in place as shown. FIG. 9B shows yet a further alternative fixation modality, wherein disc anchors 906, which do not penetrate the outer wall of the disc, but, rather remain there within, are used to hold the device 904 in place.

Figure 9C:
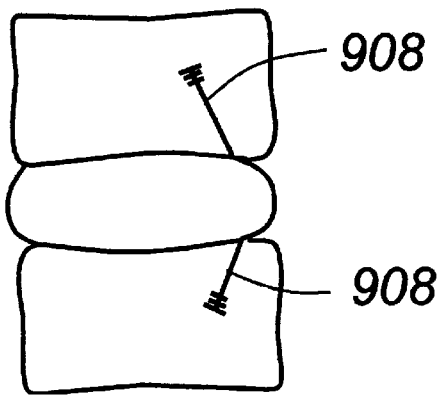
FIG. 9C illustrates an alternative method of fixation, wherein bone anchors are introduced into the vertebrae on either side of the disc in need of repair, as opposed to anchors deployed within or through the disc itself.

FIG. 9C illustrates yet a further alternative mode of fixation, wherein anchors 908 are used to hold the device to upper and lower vertebra, as opposed to the anchors of FIGS. 9A and 9B, which are used with respect to the disc. Regardless of whether fixation takes place within the vertebra or within the disc, it will be noted that according to the preferred embodiment of the invention, both the device used to occlude the defect and the fixation means are sufficiently flexible that the defect remains occluded with movement of the spine, that is, with the patient leaning forwardly and backwardly which will tend to change the spacing between the upper and lower vertebra.

Figure 10:
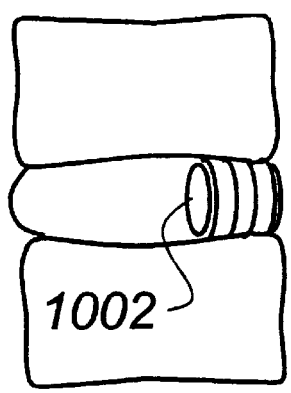
FIG. 10 illustrates an alternative device according to the invention in the form of a resilient plug.

FIG. 10 illustrates yet a different embodiment of the invention wherein, as opposed to a piece of flexible material or mesh, a resilient plug 1002 is instead utilized to occlude the disc defect. As in the case of the flexible sheath-like embodiments described above, such plugs are preferably offered in different sizes to correlate with differently sized defects.

In terms of a preferred material, a device according to the invention will therefore remain sufficiently flexible during movement while being capable of exerting continuous outward forces and withstanding repetitive compression and distraction of millions of cycles. The device would, therefore, preferably be made of a material that has these characteristics, while, additionally being radio-opaque for X-ray imaging, without producing too many unwanted artifacts in magnetic resonance imaging. A wire mesh of titanium is therefore preferable, since this has the proper X-ray/MRI characteristics while exhibiting the requisite flexibility for the cyclic flexion and extension. With respect to the embodiment of FIG. 10, a resilient, rubber-like material may be used to occlude the defect as shown in the drawing from a side-view perspective.

Figure 11A:
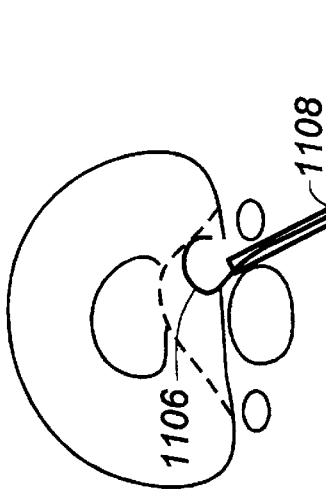
FIG. 11A illustrates an alternative embodiment of the invention wherein a coiled wire is used to occlude a disc defect.
Figure 11B:
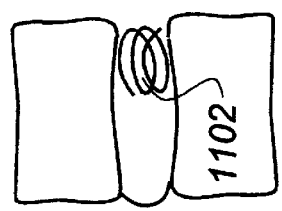
FIG. 11B is a side-view representation of the coiled wire of FIG. 11A.
Figure 11C:
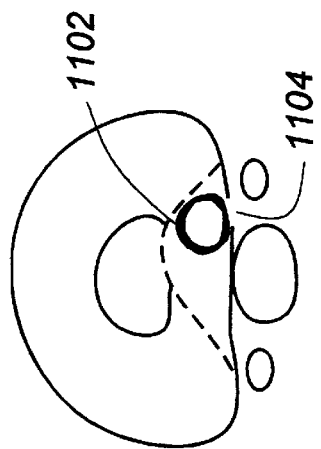
FIG. 11C illustrates how a wire with a coiled memory shape may be straightened and introduced using a plunger-type instrument.

The invention is not limited in the sense that any conformable device may be used with a first shape permitting the device to be introduced into the defective area and a second shape wherein the device includes a defect. As shown in FIGS. 11A–11C, for example, a wire 1102 having a "memory effect" may be used, preferably having a final diameter which is larger than void 1104. FIG. 11B shows the coil 1102 in cross-section between upper and lower vertebra. Preferably, this embodiment would use a metal wire that may be straightened, but retain the memory of its coiled shape. As such, the apparatus of FIG. 11C may be used to introduce the wire in straightened form 1108 with a plunger 1110, such that as the wire exits at 1106, it returns to its memorized state of a coil (or alternative second shape operative to include the defect).

Figure 12:
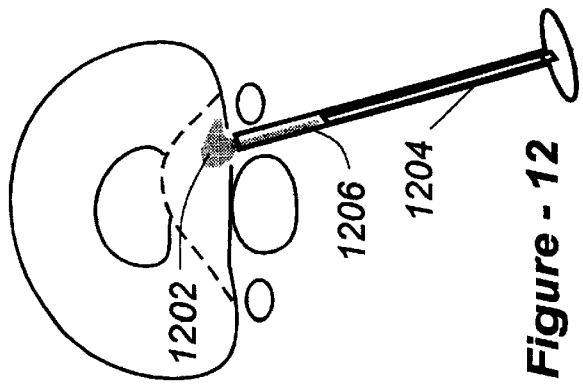
FIG. 12 illustrates yet a different alternative embodiment of the invention wherein a material in liquid or gel form may be introduced into a defect, after which it hardens or solidifies to prevent further rupturing.

As yet a different alternative mode of introduction, a material may be injected into the disc in liquid form, then allowed to hardened into a size sufficient to occlude the annular hole. As shown in FIG. 12, material 1202 may be injected into the void of the disc space using a plunger 1204 inserted into a tube 1206. Upon introduction in this manner, the liquid would then solidify, forming a resilient plug.

Various materials may be utilized for this purpose, including various polymers which are caused to solidify by various means, including thermal or optical activation, or chemical reaction as part of multi-part compounds. A preferred material with respect to this embodiment would be a hydrogel. Hydrogels may be placed into the disc in a dehydrated state, and, once inside the disc, they imbibe water. After hydration, hydrogels have the same biomechanical properties as a natural nucleus and, in addition, as the hydrogels swell, they become too large to extrude back through the annular window. U.S. Pat. Nos. 5,047,055 and 5,192,326 provide a listing of hydrogels, certain of which are applicable to this invention.

An elastomer may be used as an alternative to a hydrogel or other material. A number of elastomers may be suited to the invention, including a silicon elastomer, which comprises a cured dimethylsiloxane polymer and Hexsyn, having a composition of one-hexane with three to five percent methylhexaiene. A preformed elastomer may be inserted into the inclusion upon curing or, alternatively, as discussed with reference to FIG. 12, may be injected into the disc space and liquid form. Chemicals may be added to accelerate curing, as discussed above, or, a hot or cold probe, or UV light may be introduced to facilitate or accelerate the curing process. Preferably, such materials would include a radio-opaque additive which would enable the physician to verify the position of the implant with an X-ray. Ideally, the radio-opaque additive would not change the mechanical properties of the gel or elastomer, and would ideally incorporate-contrast throughout to enhance detail.

Figure 13A:
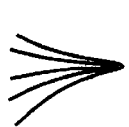
FIG. 13A illustrates yet a further alternative embodiment of the invention, in the form of a stent having a plurality of leaves.
Figure 13B:
FIG. 13B illustrates the alternative of FIG. 13A, wherein the leaves assume a second shape associated with defect occlusion, preferably through memory affect.
Figure 14A:
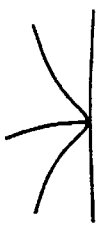
FIG. 14A illustrates an aspect of the invention wherein a conformable device is suspended within a gel or other resilient material for defect occlusion.
Figure 14B:
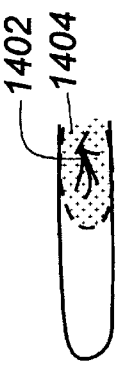
FIG. 14B is a side-view drawing of the embodiment of FIG. 14A.

Now making to FIGS. 13 and 14, FIGS. 13A and 13B illustrate an alternative type of stent having leaves or other appendages that may be folded into a compact state for insertion, FIG. 13A, and which expand, through memory affect, for example, to a state such as that shown in FIG. 13B. A stent such as this, as well as other devices disclosed herein such as the coil form of FIG. 11, may be used in conjunction with a gel or other void-filling material as described above. As shown in FIG. 14A, a stent 1402 of the type shown with respect to FIG. 13B, may be introduced into the void, after which the remaining volume of the void may be filled with a material 1404 which solidifies into a resilient material. FIG. 14B is a side-view drawing of the embodiment of FIG. 14A. An expandable stent of this kind may be incorporated into the elastomer or other resilient material to help prevent migration of the prosthesis through the annular hole. In contrast to embodiments of the invention wherein a stent is used independently, in this particular embodiment, the stent would preferably not touch vertebra, since it would be surrounded entirely by the elastomer or other gel material.

Figure 15B:
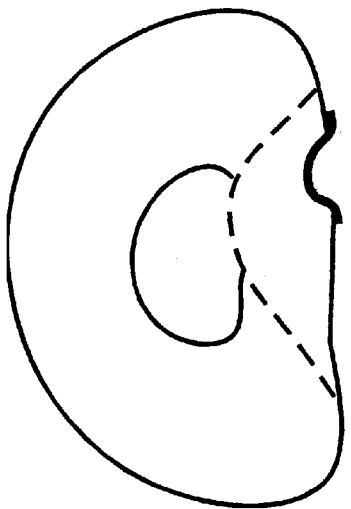
FIGS. 15A–15E are drawings which show various different alternative embodiments according to the invention wherein a patch is used inside and/or outside of a void in need of occlusion.
Figure 15A:
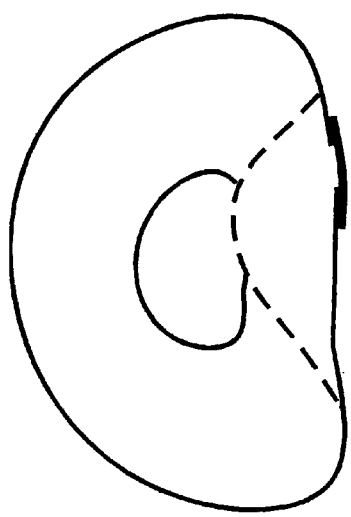
Figure 15E:
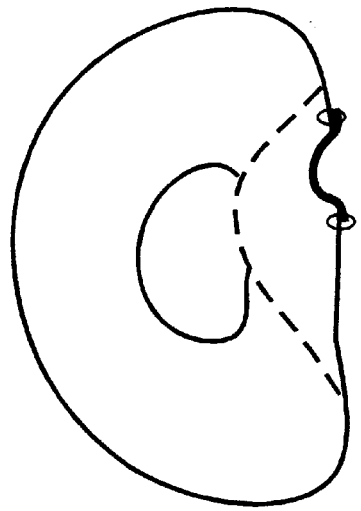
Figure 15D:
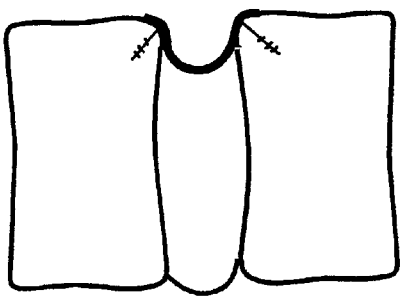
Figure 15C:
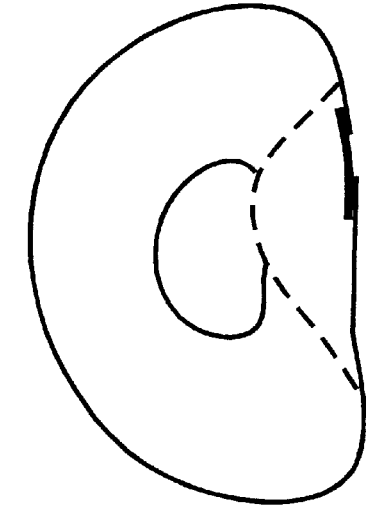

FIGS. 15A–15E illustrate various alternative embodiments according to the invention wherein a patch material is used inside, outside, or partially inside and outside of a defect to be blocked. FIG. 15A illustrates a flat patch attached onto the outside of the disc. FIG. 15B illustrates a patch attached on the outside but wherein a central portion extends inwardly into the void. FIG. 15C illustrates a patch disposed within the disc to block the defect. FIG. 15D illustrates how a patch may be anchored to the bone above and below the disc, and FIG. 15E illustrates how the patch may be anchored to the disc itself. The patch material be a fiber, including natural materials, whether human, non-human or synthetic; an elastomer; plastic; or metal. If a fiber material is used, it may be selected so as to promote tissue in-growth. Growth of a patient's tissue into the material would assure a more permanent closure of the annular window. The patch may be attached within appropriate means, including stitches, staples, glue, screws or other special anchors.

I claim:

1. A method of treating disc herniation, which involves the escape of nucleus pulposus through a defective region in the annulus fibrosis of a disc situated between upper and lower vertebra, the method comprising the steps of:
   providing a conformable device having a contracted shape with a dimension smaller than the defective region and an expanded shape with a dimension at least as large as the defective region;
   inserting the device into the region of the defective region in the annulus fibrosis when the device is in the contracted shape; and
   causing or allowing the device to expand into the expanded shape to become lodged at least partially in the defective region of the annulus fibrosis, thereby occluding the defective region and preventing the escape of the nucleus pulposus therethrough.

2. The method of claim 1, wherein the device is a body of resilient material.

3. The method of claim 1, wherein the device is a patch or mesh screen.

4. The method of claim 3, further including the steps of:
   collapsing the patch or screen into an elongated first shape;
   pushing the collapsed patch or screen into the defective region using an insertion tool; and
   removing the tool.

5. The method of claim 4, wherein the path or screen further includes one or more peripheral anchors.

6. The method of claim 5, further including the steps of:
   providing a distracting tool; and
   forcing the anchors into the vertebra using the distracting tool.

7. The method of claim 1, further including the steps of:
   providing the device according to the first shape in the form of a liquid or gel which solidifies into a resilient material; and
   injecting the liquid or gel into the defective area prior to hardening.

8. The apparatus of claim 7, wherein the device is a hydrogel.

9. The apparatus of claim 7, wherein the device is an elastomer.

10. The method of claim 1, further including the steps of:
    providing the device in the form of an elongated element having a memory of the second shape; and
    straightening the elongated element for introduction into the defective area, whereupon it assumes the second shape due to the memory effect.

11. The method of claim 10, further including the steps of:
    providing a plunger mechanism having a tube with a distal opening operative to hold the device in the straightened form; and
    applying pressure to the plunger so as to push the device out of the tube, whereupon it assumes the second shape through memory effect.

12. The method of claim 1, further including the step of injecting a liquid or gel into the defective area which solidifies with the device expanded therein.

13. The method of claim 12, wherein the step associated with providing a conformable device includes providing a device incorporating a radio-opaque contrast material.

14. The method of claim 1, wherein the step associated with providing a conformable device includes providing a device incorporating a radio-opaque contrast material.

* * * * *